(12) United States Patent
Armgart et al.

(10) Patent No.: US 10,350,551 B2
(45) Date of Patent: Jul. 16, 2019

(54) METHOD AND DEVICE FOR CARRYING OUT AN INTEGRITY TEST ON A FILTER ELEMENT

(71) Applicant: Sartorius Stedim Biotech GmbH, Goettingen (DE)

(72) Inventors: Dieter Armgart, Moringen (DE); Dirk Leiser, Braunschweig (DE); Vanessa Rakebrandt, Adelebsen (DE); Juergen Van Den Boogaard, Dransfeld (DE)

(73) Assignee: Satorius Stedim Biotech Gmbh (DE)

( * ) Notice: Subject to any disclaimer, the term of this patent is extended or adjusted under 35 U.S.C. 154(b) by 251 days.

(21) Appl. No.: 15/325,155

(22) PCT Filed: Aug. 26, 2015

(86) PCT No.: PCT/EP2015/001740
§ 371 (c)(1),
(2) Date: Jan. 10, 2017

(87) PCT Pub. No.: WO2016/030013
PCT Pub. Date: Mar. 3, 2016

(65) Prior Publication Data
US 2017/0189858 A1    Jul. 6, 2017

(30) Foreign Application Priority Data
Aug. 29, 2014    (DE) .......................... 10 2014 012 784

(51) Int. Cl.
*B01D 65/10* (2006.01)
*B01D 71/36* (2006.01)
(Continued)

(52) U.S. Cl.
CPC ........... *B01D 65/102* (2013.01); *B01D 71/36* (2013.01); *G01F 15/125* (2013.01);
(Continued)

(58) Field of Classification Search
CPC ............ B01D 65/102; G01N 15/0826; G01N 2015/084; G01N 2015/086; G01F 15/125
See application file for complete search history.

(56) References Cited

U.S. PATENT DOCUMENTS

| | | | |
|---|---|---|---|
| 5,353,630 | A | 10/1994 | Soda et al. |
| 5,786,528 | A | 7/1998 | Dileo et al. |

(Continued)

FOREIGN PATENT DOCUMENTS

| | | |
|---|---|---|
| DE | 36 18 112 | 12/1986 |
| DE | 41 12 878 | 10/1992 |

(Continued)

OTHER PUBLICATIONS

International Search Report dated Dec. 11, 2015.
German Examination Report dated May 6, 2015.

*Primary Examiner* — Paul M. West
(74) *Attorney, Agent, or Firm* — Gerald E. Hespos; Michael J. Porco; Matthew T. Hespos

(57) ABSTRACT

A method for carrying out an integrity test on a filter element includes filling a fluid into at least one vessel (1), in which a filter element (F) to be tested is arranged. The method proceeds by setting the pressure of the fluid in the vessel (1) to a predetermined test pressure, and maintaining the test pressure in the vessel (1) with controlled replenishment of fluid into the vessel (1) and/or a controlled change in internal volume of the vessel (1). The method continues by determining an integrity characteristic variable for the filter element (F) in a manner dependent on the controlled replenishment of fluid into the vessel (1) and/or dependent on the controlled change in internal volume of the vessel (1) before attaining a substantially continuous volume flow of fluid for maintaining the specific test pressure in the vessel (1).

18 Claims, 5 Drawing Sheets

(51) Int. Cl.
*G01F 15/12* (2006.01)
*G01N 15/08* (2006.01)

(52) U.S. Cl.
CPC ... *G01N 15/0826* (2013.01); *G01N 2015/084* (2013.01); *G01N 2015/086* (2013.01)

(56) References Cited

U.S. PATENT DOCUMENTS

2003/0234211 A1    12/2003  Seiler et al.
2012/0059603 A1*   3/2012   Stering .............. B01D 46/0086
                                                        702/47
2014/0298893 A1    10/2014  Laubstein et al.

FOREIGN PATENT DOCUMENTS

| DE | 195 03 311      | 8/1996 |
| DE | 102 27 160      | 1/2004 |
| DE | 10 2011 111 050 | 2/2013 |
| EP | 2 425 886       | 3/2012 |
| JP | 4-131729        | 5/1992 |
| JP | H0894514 A      | 4/1996 |
| JP | 2005032934 A    | 2/2005 |
| WO | 2013/026507     | 2/2013 |

\* cited by examiner

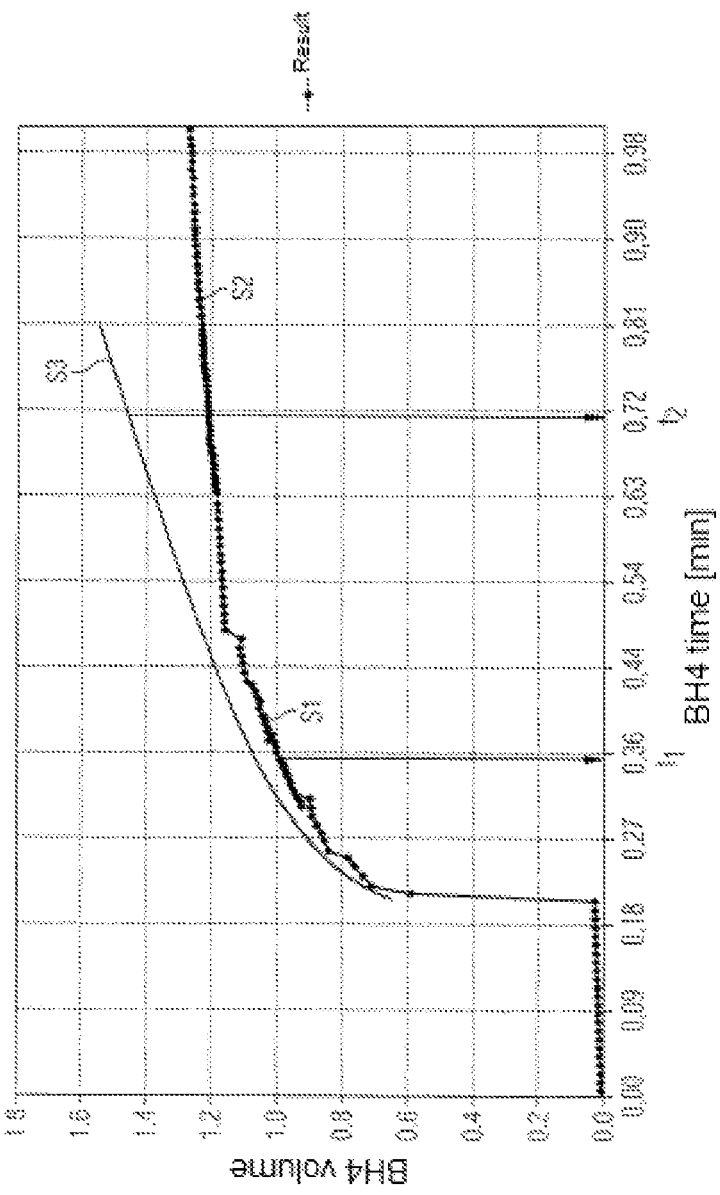

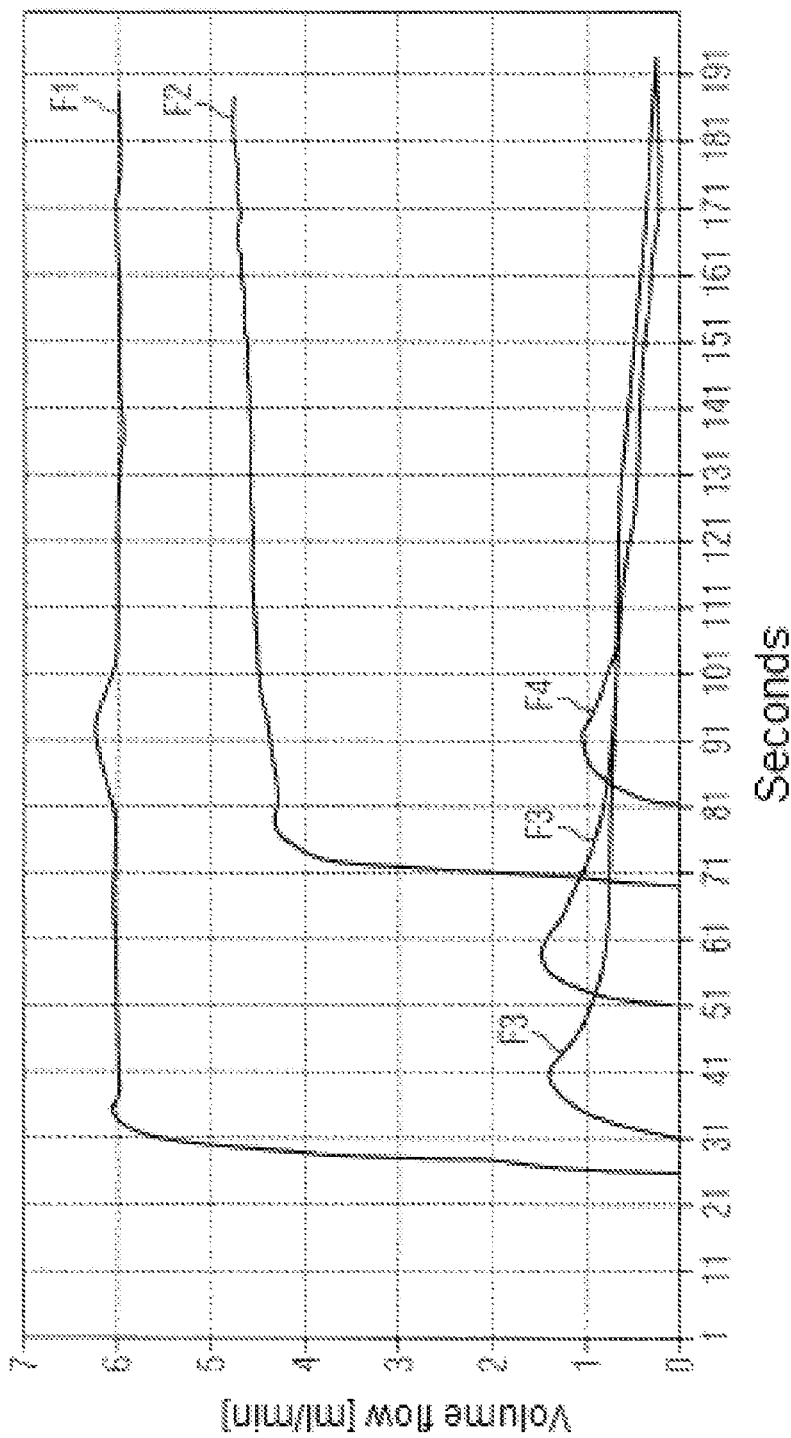

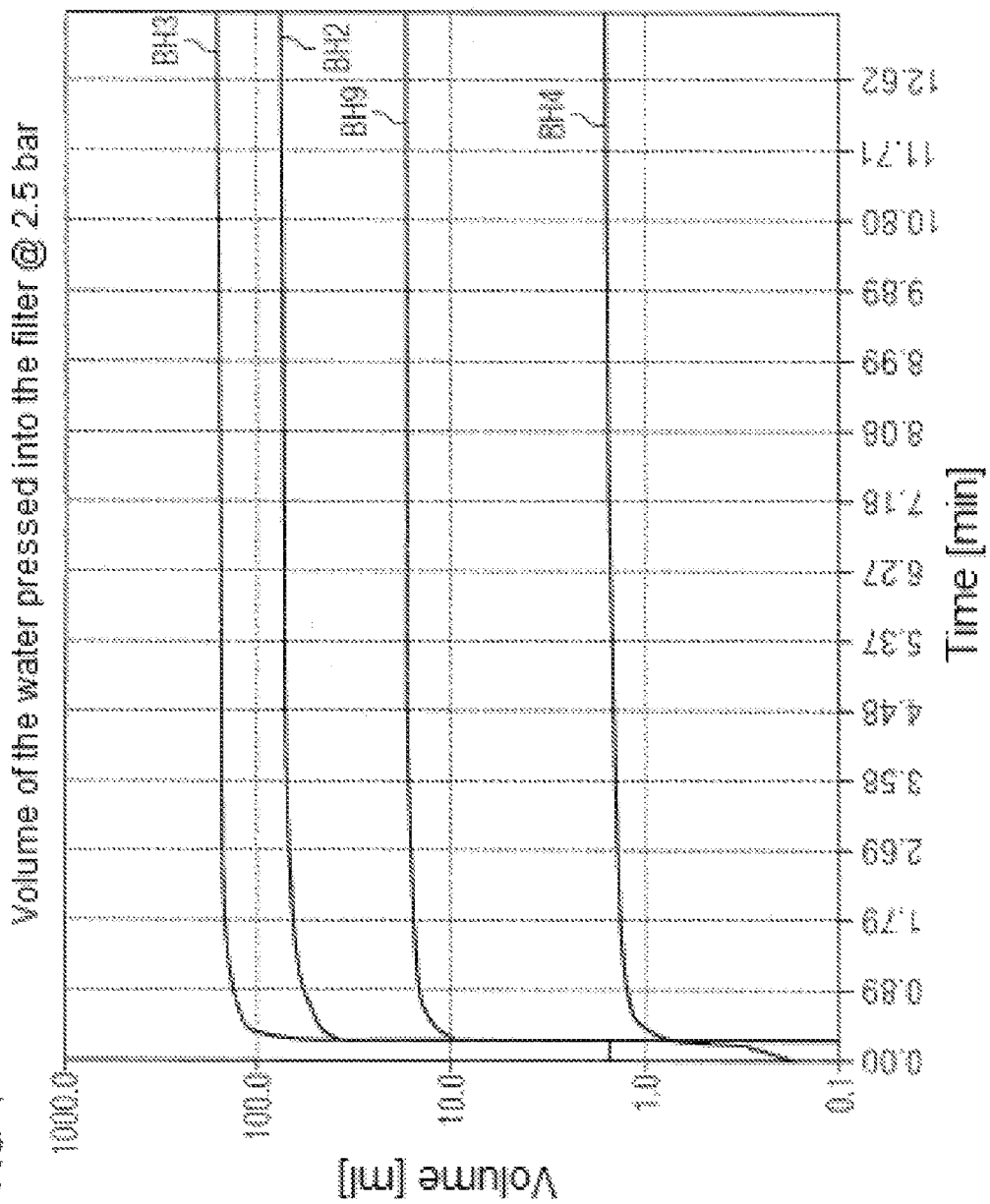

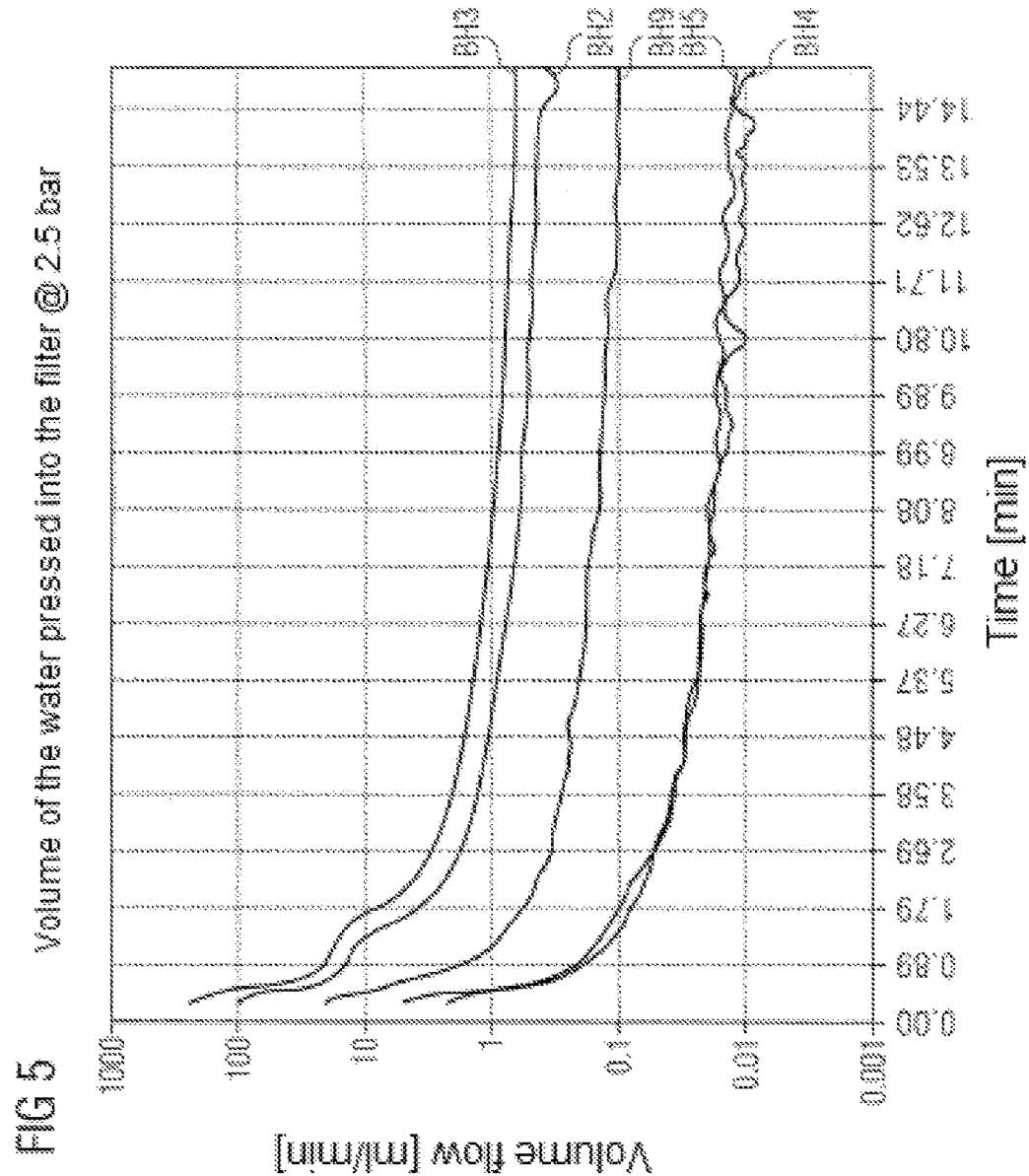

METHOD AND DEVICE FOR CARRYING OUT AN INTEGRITY TEST ON A FILTER ELEMENT

BACKGROUND

1. Field of the Invention

The present invention relates to a method and a device for testing the integrity of filter elements, in particular filter elements for sterile filtration.

2. Description of the Related Art

Filtration systems for sterile filtration of gases and liquids are employed in many areas of technology, in particular in the pharmaceutical industry, food production, the electronics industry etc. Sterile filters with membranes made of different polymers are employed for sterile filtration. In the sterile filtration of gases and in the sterile ventilation from vessels, in particular in the pharmaceutical industry, standard sterile filters with hydrophobic membranes such as, for example, membranes based on polytetrafluoroethylene (abbreviated to PTFE) are employed.

Conventional methods of testing hydrophobic filter elements are either wetted with alcohol and measured at diffusion/bubble point in the single-digit minute range with the known disadvantages of subsequent drying. In a second test method water pressure is applied to the hydrophobic filters and testing for water flow or water intrusion is performed in the double-digit minute range. Only filter surfaces greater than or equal to 900 cm2 can be measured with the WFT and WFI. Smaller filter surfaces must be wetted with alcohol with the known disadvantages.

Previous testing technologies in the single-digit minute range for sterile filters are based on measurement of a pressure rise on an outlet side or measurement of a pressure drop on an inlet side of a pleated PTFE filter element wetted with an isopropanol/water mixture. With a given volume, a diffusion through the filter element can be calculated from the measured pressure rise or pressure drop. This testing technology is regarded as an indirect testing method and has the disadvantages that the testing method is temperature-dependent and requires a reference volume for carrying out the measurement. Furthermore, the known method has the disadvantage that the filter element must be wetted with alcohol for the measurement. As a result, a final drying process in explosion-proof drying cabinets is necessary, which can last for approximately 8 hours.

A testing method which omits the use of alcohol is the so-called water flow test (abbreviated to WFT). In this case wetting of the filter element with alcohol can be omitted if RO water is used as the testing medium. RO water is completely desalinated water. Because of the hydrophobicity of PTFE, the filter element is largely dry after the completion of the testing process, so that the subsequent drying process can be significantly shortened.

In the WFT the PTFE filter element is positioned in a vessel which has been completely filled at the inlet end with RO water. During the test process a test pressure is built up by means of the RO water below a filter-specific intrusion pressure of water which leads to a pressure drop in a previously determined reference volume. The quantity of RO water which has been pressed through the membrane of the PTFE filter element in a predetermined time interval is calculated from the measured pressure drop. In order to produce a measurable pressure drop, testing times in the double-digit minute range of usually 23 minutes per test-piece are necessary, which is why the WFT method is not suitable for an industrial scale and is not suitable for testing very small filter elements. The WFT method is temperature-dependent and determines the integrity of the filter element to be tested only indirectly by means of a previous net volume measurement.

The object of the invention is to enable improved integrity testing of filter elements. In particular, the disadvantages of the WFT method such as, for example, the long measurement time, the limited accuracy of measurement and/or the restricted field of application should be reduced.

SUMMARY

One aspect relates to a method for carrying out an integrity test on a filter element, comprising the steps of:
  filling at least one vessel, in which a filter element to be tested is arranged, with a fluid,
  setting the pressure of the fluid in the vessel to a specific (predetermined or predeterminable) test pressure,
  maintaining the specific test pressure in the vessel with controlled replenishment of fluid into the vessel and/or with a controlled change in internal volume of the vessel,
  determining an integrity characteristic variable for the filter element in a manner dependent
  on the controlled replenishment of fluid into the vessel and/or in a manner dependent
    on the controlled change in internal volume of the vessel before a substantially continuous volume flow of fluid, which is required for maintaining the specific test pressure in the vessel, arises.

Thus a test method is provided by which a WFT in the single-digit minute range can be carried out and by which, moreover, it is also possible to test filter surfaces which are smaller than 900 cm2.

This method is used to check the integrity of the at least one filter element which can be formed, in particular, as a PTFE filter element and/or sterile filter element of the type described in the introduction. The vessel can be filled at the inlet end with the fluid. The filter element can be arranged in the vessel at the discharge end so that the fluid only leaves the vessel after the fluid has penetrated the filter element, for example by evaporation. An additional outlet valve can be provided in order to be able to drain off the fluid from the vessel in the event of interruption and/or after the end of the integrity test.

The fluid used therefor may be an aqueous fluid such as, for example, RO water, that is to say completely desalinated water. In the method, first of all the vessel is at least partially filled with the fluid. The filling operation can take place, in particular, with a specific (predetermined or predeterminable) filling pressure, which is less than the specific (predetermined or predeterminable) test pressure.

During adjustment of the fluid a specific (predetermined or predeterminable) test pressure is set in the vessel, wherein compacting of the filter element begins. This can take place, for example, by supplying compressed air to the fluid. In this case the specific (predetermined or predeterminable) test pressure which is lower than the intrusion pressure of the filter element. The specific (predetermined or predeterminable) test pressure can be adapted to the filter element and thus can be predetermined in a filter-specific manner.

During the setting a rough leak test can already be carried out. In this case it is checked whether the filter element allows a predetermined quantity of fluid to pass through, which already during compacting of the filter element leads to the conclusion that the filter element will not pass the integrity test. In this case the integrity test of the filter element can be interrupted. During compacting of the filter element, a particularly large amount of fluid can be pressed through the filter element, particularly when the filter element is damaged and thus has a reduced intrusion pressure.

In the method, during the determination of the integrity characteristic variable the specific (predetermined or predeterminable) test pressure is maintained in the vessel. Since during the determination of a certain small quantity of fluid penetrates through the filter element, this quantity of fluid is either replenished in the vessel or the internal volume of the vessel is decreases, in order to obtain the specific (predetermined or predeterminable) test pressure in the vessel. Thus in several exemplary embodiments both a controlled replenishment of fluid and also a controlled changing of the internal volume of the vessel can be provided and carried out.

In this case changing the internal volume of the vessel means that the internal volume available for the fluid in the interior of the vessel is changed, in particular reduced in a controlled manner.

This replenishment of fluid and/or changing of the internal volume of the vessel takes place in a controlled manner. This means that it is possible to check precisely how much fluid must be replenished into the vessel and/or in order by how much the internal volume of the vessel must be changed (in particular reduced) in order to maintain the predetermined test pressure therein. Thus during the replenishment and/or changing of the internal volume it is possible, for example, to determine the quantity (and/or the volume) of fluid which passes through the filter element when the specific (predetermined or predeterminable) test pressure is determined. Alternatively, another measured value can also be determined which is dependent upon this quantity of fluid, such as, for example, the number of incremental steps of a controller, which replenishes the fluid in the vessel and/or effects the changing of the internal volume. The internal volume of the vessel can be changed, for example, by penetration and/or introduction of a displacement body into the interior of the vessel. The depth of penetration of the displacement body into the interior can be activated and/or controlled, for example, by a controller. The volume of the displacement body which is introduced into the interior of the vessel at a selected time corresponds to the total volume of fluid which has passed through the filter element since the start of the test.

Thus while the predetermined test pressure is maintained, the integrity characteristic variable for the filter element is simultaneously determined. In this case the integrity characteristic variable can comprise any entity characterizing the integrity of the filter element, such as, for example, a variable, a flag, a number, a value and/or a logic indicator. The integrity characteristic variable can depend upon the continuous volume flow of fluid required in order to maintain the specific (predetermined or predeterminable) test pressure. In this case, for example, a volume flow through the filter element, a change of the volume per unit of time, a change of the volume flow (that is to say, the second derivative of the volume with respect to time), and/or a number of incremental steps can be determined and/or evaluated as an integrity characteristic variable.

Additionally, for example, the temperature of the fluid can be measured by means of a temperature sensor in order to carry out the integrity test independently of the temperature. The pressure, the absolute volume and the temperature can also be measured at the same time.

In this case the aim of the method is not necessarily the measurement of an exact integrity characteristic variable, that is to say, for example, the measurement of the exact continuous volume flow which occurs. The method may merely lead to the conclusion as to whether the filter element will or will not pass the integrity test. This can include the conclusion as to whether or not the predicted or estimated integrity characteristic variable will lie below a filter-specific and/or pre-defined integrity limit value for the filter type to be tested.

In this case the integrity characteristic variable for the filter element is determined before the occurrence of a substantially continuous volume flow of fluid which is required for maintenance of the specific test pressure in the vessel. Often 23 or more minutes pass before the occurrence of the continuous volume flow, which (as described in the introduction) leads to long testing times. In the method, however, the determination of the integrity characteristic variable takes place substantially earlier, i.e. already while the volume flow is still changing.

In this case a "substantially constant volume flow" means that the volume flow hardly changes. This may in particular mean that the volume flow changes at most by 20% per minute, preferably changes at most by 10% per minute, particularly preferably changes at most by 5% per minute, particularly preferably changes by at most 1% per minute. A substantially constant volume flow regularly occurs as soon as the filter element is compacted.

According to one embodiment the integrity characteristic variable is dependent upon at least one characteristic of the volume flow of fluid which is required for maintenance of the specific test pressure in the vessel. The characteristic may be, for example, a first and/or second derivative of the volume flow with respect to time. The characteristic is dependent upon the change of the volume flow. The characteristic of the volume flow for the filter element to be tested can be compared with a predetermined value of the characteristic for the volume flow to be expected under the specific test pressure for a filter element of the same type or the same construction. If the volume flow determined and/or estimated by means of the characteristic deviates too much from the predetermined value for the filter type, the tested filter element does not pass the test. If the volume flow determined and/or estimated by means of the characteristic deviates too much from the predetermined value for the filter type, the tested filter element does not pass the test.

According to one embodiment the integrity characteristic variable is determined before the filter element is compacted. The compacting of the filter element can already begin with the introduction of the fluid. However, the compacting of the filter element is only concluded after a certain time period, for which the fluid is held in the vessel at the specific test pressure of, for example, 2.5 bars. A continuous volumetric flow through the filter element only takes place after this. In the case of conventional measurements, the compacting of the filter element is concluded as far as possible approximately 10 minutes after the start of the introduction of the fluid. With the method the integrity characteristic variable of the filter element is already determined before this time, that is to say while the filter element is being further compacted.

According to one embodiment the integrity characteristic variable is determined within a maximum of nine minutes after the start of filling of the vessel, preferably within a maximum of five minutes. This short time period in the single-digit minute range is already sufficient in order to estimate the continuous volumetric flow taking place through the filter element, even if this usually only takes place after approximately 23 minutes.

According to one embodiment the controlled change in internal volume of the vessel takes place by means of a displacement body which penetrates and/or can be introduced into the vessel. In this case the maintenance of the test pressure is effected directly in the vessel by the displacement body, of which the penetration volume determines the volume of fluid which has become smaller due to compacting and evaporation. The displacement body can be configured, for example, as a displacement piston, in particular as a displacement piston of a pressure measurement cell which penetrates into the interior of the vessel in a controlled manner. In this embodiment a pressure measurement cell which provides the displacement body can be integrated into the test vessel.

According to one embodiment the controlled replenishment of fluid into the vessel takes place by means of a pressure measurement cell. Alternatively, or in addition, the change of the internal volume of the vessel can take place by means of a pressure measurement cell which is integrated internally into the vessel. The pressure measurement cell can, on the one hand, maintain the predetermined test pressure in the vessel and, on the other hand, while the test pressure is maintained it can measure the volume of fluid which is required for this purpose. The measurement takes place with a precision of approximately 0.1 µl to approximately 10 µl, preferably from approximately 1 µl to approximately 5 µl. For this purpose, a certain fluid volume, which can be dispensed to the first vessel during the method step of maintaining the test pressure, can be pre-stored in the pressure measurement cell.

In this case by means of a stepping motor of the pressure measurement cell a pressure piston can be actuated so that the specific test pressure is maintained in the vessel. The stepping motor can be configured, in particular, as a precision stepping motor integrated into the pressure measurement cell. Instead of a pressure drop at a net volume in the vessel, by means of a cylinder of the pressure piston filled with the fluid and with the aid of the stepping motor the specific test pressure is maintained as the target pressure in the vessel. The volume difference which occurs is compensated for and determined and/or evaluated. By means of the number of increments of the stepping motor required for compensation and the dimensions of the cross-section of the pressure piston, i.e. for example the cylinder cross-section thereof, the volume flow required for compensation, for example, can be determined.

According to one embodiment the integrity characteristic variable is determined by a mathematical estimation. In this case it is, for example, estimated what continuous volume flow of the fluid occurs if the specific test pressure is maintained in the vessel. In this case the volume which is introduced into the vessel in order to maintain the test pressure can be measured directly per unit of time. Thus the method is a direct testing method in which the volume flow can be directly measured.

The estimation can take place in such a way that for each measurement time a sliding incremental volume flow, i.e. a slope of the volume characteristic, is calculated from the individual measured values for volume and time. The curve shape of the volume characteristic over time is normally degressively falling. In addition to the sliding volume flow, the sliding time derivative of the volume flow, i.e. the curvature of the volume characteristic, can be calculated. As soon as the time derivative of the volumetric flow, that is to say the curvature of the volume characteristic, approaches zero, this can be used as a measure for the integrity of the first filter element to be tested, i.e. for example as an integrity characteristic variable. The continuous volume flow which occurs serves as a measure, characteristic value or characteristic quantity for the integrity and thus for the quality of the filter element.

It usually takes a long time until a continuous volume flow occurs. The operation can in particular extend over a time period of several hours. In order to shorten the testing time, the evaluation of the filter element as testpiece takes place at a significantly earlier time, and specifically the integrity test is ended long before the continuous volume flow is exactly determined. For carrying out the integrity test it is sufficient, for example, to estimate mathematically what continuous volume flow is expected. The estimation can take place, for example, with reference to a characteristic of the volume flow and by means of different mathematical methods for estimation of the curve evolution. Already after a few minutes a sufficiently precise estimation can take place by the evaluation of the measured values.

Thus the estimation can, in particular, include a prediction.

According to one embodiment the integrity test is ended when the estimation shows that with a predetermined probability the filter element to be tested will or will not pass the integrity test. Thus for estimation a prediction as to whether or not the integrity test will probably be passed is sufficient. Exact determination of the continuous volume flow which occurs as test value or integrity characteristic variable for the integrity test is not necessary. The method can already be interrupted if, with a predetermined probability, the integrity characteristic variable or the predicted continuous volume flow lies within a predetermined limit value.

According to one embodiment the estimation takes place by a mathematical prediction of a volume flow of the fluid which occurs by means of enveloping curves, wherein the enveloping curves are coordinated with the filter element to be tested. In this case the volume flow and/or the change of volume flow can be compared with limit values predetermined by enveloping curves, from which a predicted integration measurement value can be determined for the expected volume flow of the fluid which occurs, in order to maintain the predetermined test pressure in the vessel. In this case the position and the mathematical description of the enveloping curves can be characteristic for the filter type of the filter element in question. In this case the enveloping curves can be ascertained and predetermined on the basis of preceding measurements on this filter type, for example with a 95% percentile. In this case an evaluation time of the filter element to be tested may depend upon the extent to which the currently determined measured values lie, with respect to their level and the curve shape, within the defined enveloping curves and enable a prediction of the final integrity characteristic variable.

In this case the start of the measurement may be dependent upon the stability and compacting behavior of the filter element to be tested, but can be enforced if a compacting time which is the maximum tolerable time in terms of productivity is exceeded.

According to one embodiment the integrity test is carried out on a plurality of different filter elements with method steps overlapping one another in time. In this case the individual method steps are separated from one another and in particular can be carried out separately from one another. Thus the testing time per filter element tested is decreased, since several filter elements can be tested at the same time, in particular three filter elements at the same time.

In a further development of this embodiment, while the specific (predetermined or predeterminable) test pressure is maintained in a first vessel with a first filter element to be tested with controlled replenishment of fluid:

fluid in a second vessel, in which a second filter element to be tested is arranged, is set to the specific (predetermined or predeterminable) test pressure and fluid is introduced into a third vessel in which a third filter element to be tested is arranged.

Thus the method steps of filling, setting and maintaining pressure are carried out, chronologically staggered relative to one another, on three different vessels with three different filter elements. The method steps are carried out in a chronologically staggered manner: The method begins with the filling of the first vessel. Next the pressure in the first vessel is set while the second vessel is filled. While the test pressure is maintained in the first vessel, at the same time the pressure in the second vessel is set and the third vessel is filled. Next the specific (predetermined or predeterminable) test pressure is maintained in the second vessel, while the pressure in the third vessel is set. In the last step the specific (predetermined or predeterminable) test pressure is maintained in the third vessel.

The method steps can be carried out, chronologically staggered, at three different test stations each having one filter element to be tested. In this case the method step at one test station can always be reclocked synchronously with the method steps at the two other test stations, wherein the most time-critical method step in each case with the longest process time is the clock generator for reclocking of the method steps. Thus in each process phase it is ensured that only one single line to the respective vessel is opened, namely the line which is associated with the respective method step. This can be ensured, for example, by the use of controllable three-way valves, for example, by use of Robolux valves, by means of which in each case one of three different conduits can be connected to the vessel. As a result, on each vessel a fast reclocking, virtually free of dead spaces, between the method steps is ensured. Furthermore, interactions between the test stations can be avoided.

In a further development of this embodiment the controlled replenishment of fluid into the vessel takes place with a precision of less than approximately 10 µl.

One aspect relates to a device for carrying out an integrity test on a filter element with a vessel in which a filter element to be tested can be arranged, the device comprising at least one conduit, by which a fluid can be introduced into the vessel so that the pressure of the fluid can be set to a specific (predetermined or predeterminable) test pressure, a fluid feed, which maintains the specific (predetermined or predeterminable) test pressure in the vessel by replenishing the fluid feed into the vessel in a controlled manner and/or changes the internal volume of the vessel in a controlled manner, and an evaluation means which, in a manner dependent on the controlled replenishment of fluid into the vessel and/or in a manner dependent on the controlled change in internal volume of the vessel, an integrity characteristic variable for the filter element is determined before a substantially continuous volume flow of fluid occurs, which is required for maintaining the specific test pressure in the vessel.

The device can have, instead of one single line, for example, a filling conduit for filling of the vessel as well as a compacting conduit for setting the pressure of the fluid in the vessel. In this case the filling conduit can be connected, for example, to a source of RO water by means of which RO water can be introduced into the filling conduit. The filling of the vessel can take place from the bottom upwards, in order to enable turbulence-free filling and safe ventilation. The filling can be ended when a filling level sensor at the outlet of an air-vent conduit makes contact with water and closes an intake by means of a valve, so that the filling conduit can again be separated from the vessel. The air-vent conduit can be fitted with a slight slope, so that it empties in the direction of the slope. This type of filling can make it possible that during the filling operation no pressure occurs above the specific (predetermined or predeterminable) test pressure.

The filter element can be arranged in the vessel at the discharge end so that the fluid only leaves the vessel after the fluid has penetrated the filter element, for example by evaporation.

The evaluation means can, for example, have a processor, such as for example a PC. The evaluation means can be programmed so that it determines the integrity characteristic variable for the filter element to be tested, for example by estimation of a continuous volume flow of fluid which occurs in order to maintain the specific (predetermined or predeterminable) test pressure in the vessel. This estimation takes place before the occurrence of a substantially continuous volume flow of fluid. In this case a substantially continuous volume flow can be regarded as a volume flow of which the incremental change per unit of time (or the first derivative thereof) is below a specific (predetermined or predeterminable) threshold value (for example, less than approximately 1% of the corresponding volume flow). Furthermore, it is possible to regard a substantially continuous volume flow as a volume flow which occurs after a sufficient time (for example after more than approximately 20 minutes) on a reference filter having integrity.

The fluid feed is formed as a fluid feed to the filter element. In this case the fluid feed can be formed outside the vessel as an external fluid feed (for example, as a pressure measurement cell) which feeds fluid via a conduit to the filter element arranged in the vessel. Alternatively, or additionally, the fluid feed can be formed as an internal fluid feed, for example as a displacement body, which can be introduced and/or inserted into the interior of the vessel.

An internal fluid feed has the advantage that no conduits have to be provided between the internal fluid feed and the vessel, since the displacement body can be formed, for example, at a location on the vessel wall so that it can be introduced and/or inserted through the vessel wall into the interior of the vessel. In this case the displacement body can be designed to be passed in a fluid-tight manner through the vessel wall.

An internal fluid feed can be simply cleaned and/or steamed.

In an alternative embodiment of an external fluid feed a displacement body can be arranged at any position outside the vessel in physical contact with the fluid so that the displacement body reduces the fluid volume in a controlled manner before penetration of the filter element. The fluid thus displaced is fed to the vessel, for example, by means of a conduit.

In one embodiment the evaluation means estimates the integrity characteristic variable in dependence upon at least one characteristic of the volume flow of fluid which is required for maintenance of the specific test pressure.

According to one embodiment the fluid feed replenishes fluid into the vessel with a precision of approximately 0.1 µl to approximately 10 µl and/or changes the internal volume of the vessel preferably with a precision of approximately 0.1 µl to approximately 5 µl. This precision influences the precision of the determination of the integrity characteristic variable. A pressure measurement cell as fluid feed can, for example, replenish fluid with a precision of approximately 4 μl.

In one embodiment the fluid feed is designed as a pressure measurement cell having a stepping motor which actuates a piston so that in the vessel the specific (predetermined or predeterminable) test pressure is substantially maintained. Such a pressure measurement cell can have a total volume of up to approximately 500 ml.

In this case the evaluation means can use a step number or index of the stepping motor of the pressure measurement cell as a characteristic quantity of the volume of fluid which flows through the filter element in order to maintain the specific test pressure.

In one embodiment the fluid feed is designed as a displacement body which penetrates in a controlled manner into the vessel and in this case changes the internal volume of the vessel. In this case "controlled" means that, for example, the penetration volume and/or the penetration depth of the displacement body into the vessel is controllable. In this case the displacement body can be designed as a displacement piston, for example as a displacement piston of a pressure measurement cell inside the vessel. The displacement body can be designed, for example, as a plunger cylinder which has a predetermined cylinder cross-section and can be introduced into the test vessel in a controlled manner in the direction of its cylinder axis. In such an embodiment the penetration volume of the displacement body can be determined with a precision of approximately 0.1 μl to approximately 10 μl.

According to one embodiment the device has a compacting vessel which is connected to a compacting conduit, wherein the compacting vessel is compacted to the specific (predetermined or predeterminable) test pressure. The compacting conduit can be designed and provided for setting the pressure of the fluid in the vessel to the specific (predetermined or predeterminable) test pressure. The compacting of the filter element can take place, for example, at approximately 2.5 bar, the compacting vessel being designed as a regulated storage tank. The volume of the compacting vessel is dimensioned so that it can simultaneously carry out a plurality of compacting operations, for example up to three compacting operations at the same time on three different vessels each having a filter element.

During the compacting operation or in connection with the compacting operation a gross leak test of the first filter element can take place, for example, by means of a Coreolis mass flow sensor integrated in the compacting conduit, the measurement range of which is adapted to the compacting volume of the product group to be tested, specifically of the filter element to be tested. Furthermore, the mass flow sensor makes it possible to measure, in addition to the mass flow, the density and temperature of the fluid from the compacting vessel. If the measured value of the mass flow sensor during the compacting permanently exceeds a predetermined value, i.e. the compacting does not decrease with the time progression as expected, the filter element to be tested is evaluated as a reject with a gross leak. Subsequently a changeover from compacting to maintenance of the pressure and measurement are prevented in order to avoid unwanted emptying of the pressure measurement cell during the measurement, since otherwise the pressure measurement cell would have to be topped up again.

According to one embodiment the device has a pressure reducer and/or a flow reducer, which reduces the pressure and/or the flow of the fluid in a filling conduit. The filling conduit can be designed and provided for filling the vessel with fluid. The pressure reducer and/or the flow reducer are integrated in the filling conduit or connected thereto so that they can reduce the pressure of the fluid in the filling conduit. As a result, the fluid pressure during filling of the vessel is kept below the specific (predetermined or predeterminable) test pressure which was only set during compacting. In this case the filling of the respective vessel can take place directly from the filling conduit by means of the pressure reducer which is, for example, manual and the flow reducer which is, for example, connected downstream.

According to one embodiment, the device has a controllable three-way valve, by means of which either a filling conduit, a compacting conduit or the pressure measurement cell can be connected to the vessel. In this case the controllable three-way valve is controllable so that in each case one of the three conduits of the device is connected to the vessel. The control can take place electronically and can be performed by the evaluation means. Due to the valve position of the controllable three-way valve it is ensured, that in each case only one of the three conduits is connected to the vessel, and thus the individual process steps are sufficiently separate from one another during testing of the filter element.

According to one embodiment the device has three controllable connecting valves for selective connection of either a filling conduit, a compacting conduit or the pressure measurement cell to a first vessel in which a first filter element to be tested can be arranged, to a second vessel in which a second filter element to be tested can be arranged, and to a third vessel in which a third filter element to be tested can be arranged. The three controllable connecting valves may in particular be controllable three-way valves, by which the connections of the conduits to the different vessels can be regulated. The control of the connecting valves can take place by means of the evaluation means. By the use of three controllable connecting valves three different filter elements can be tested at the same time, wherein the individual process steps can be carried out in a staggered manner with respect to one another, as described above in connection with the method. In this case the first vessel, the second and the third vessel can be formed as part of the device in which the or the filter element or elements can be used for checking. Alternatively, the device can also have only the connections to the one controllable three-way valve or the three controllable connecting valves, to which the first vessel or all three vessels with the filter elements to be tested can be connected.

One aspect relates to the use of the device according to the preceding aspect for carrying out the method according to the first aspect or a preferred embodiment thereof. Thus the device described above can be used in particular in order to carry out the method described in the introduction.

The invention is described in greater detail below with reference to an embodiment shown in one drawing. Other embodiments can include some or all of the elements shown in the drawing.

BRIEF DESCRIPTION OF THE DRAWINGS

FIG. 2 shows a diagram of a chronological development of the volume flow through a filter element.

FIG. 3 shows a diagram of a chronological development of the volume flow through five different filter elements.

FIG. 4 shows a long-term diagram of a chronological development of the fluid volume which is pressed through four different filter elements.

FIG. 5 shows a long-term diagram of a chronological development of the volume flow through five different filter elements.

DETAILED DESCRIPTION

Figure 1:
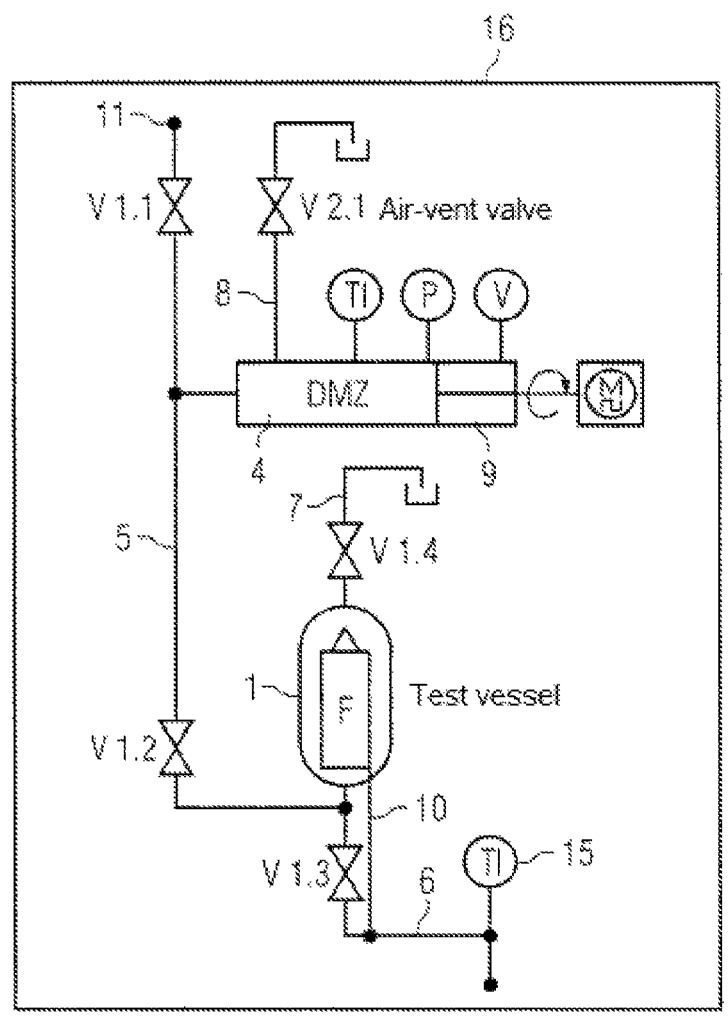
FIG. 1 shows a circuit configuration of a device for carrying out an integrity test on a filter element.

FIG. 1 shows a schematic representation of a device 16 for carrying out an integrity test on a filter element. The integrity of a filter element F arranged in a vessel 1 is checked by the device.

The device 16 is connected to a fluid inflow 11. The fluid inflow 11 is adjustable by means of a fluid inlet valve V1.1. A fluid can be introduced into a fluid conduit 5 via the fluid inflow 11. In this case RO water is preferably used as the fluid.

The fluid conduit 5 is connected to a pressure measurement cell (DMZ) 4 as a special configuration of a fluid feed. Furthermore, the fluid conduit 5 can be connected by means of a vessel valve V1.2 to the vessel 1.

The pressure measurement cell 4 can be connected to an evaluation means, which may for example be in the form of a PC. The pressure measurement cell 4 can be controlled by means of the evaluation means, in particular a pressure measurement cell controller 9 (as a special configuration of a fluid feed controller or regulator) of the pressure measurement cell 4. Furthermore, the valve positions of the device can be controlled by means of the evaluation means.

The vessel 1 has an interior which can be filled with a medium via the associated vessel valve V1.2 and the fluid conduit 5. The interior of the vessel 1 can be emptied via an outlet valve V1.3 of the vessel 1. The vessel 1 can be connected to a drain conduit 6 via the outlet valve V1.3. The temperature of the medium in the drain pipe 6 can be measured by a temperature sensor 15, which can enable maintenance and/or regulation of a minimum vapor temperature. The temperature sensor 15 is arranged on the drain conduit 6 as the coldest point of the device 16.

In the interior of the vessel 1 a filter element F is arranged so that medium diffused through the filter element F is drained out of the vessel 1 via an outlet conduit 10. This outlet conduit 10 can be connected to the drain conduit 6. In this case the fluid from the fluid conduit 5 is preferably provided as the medium.

The device 16 serves as a testing facility for carrying out a water flow test, abbreviated to WFT.

The device 16 has a test station with the vessel 1 which is associated with the pressure measurement cell 4.

The evaluation means can be configured as a supply module and/or control module and can have a power supply, a programmable logic controller (abbreviated to PLC) and/or a human machine interface (abbreviated to HMI). The evaluation unit can also be used for controlling a plurality of devices 16, wherein each device can have a vessel in each case for a filter element to be tested. Filter elements to be tested, which are formed, for example, as filter candles, have a different compacting range from filter elements which are formed, for example, as filter capsules.

The design of some or all device parts, including the sensor system, can be governed by the criterion of dry steaming capability. This means that each component of the device is designed and provided to be exposed to water vapor at a predetermined pressure, at a predetermined temperature and for a predetermined time period. The device part can be designed, for example, to be steamed at a pressure of 2.5 bars for 20 minutes at 124° C. with pure steam.

The components of the device can have valve connectors of which the maximum length corresponds to twice their internal diameter. The conduits can have a slope in order to enable complete emptying.

The device together with valve seats can be free of hollow spaces, dead spaces and/or blind holes. This reduces the danger of contamination and corrosion as a result of puddle formation in the device.

The valves used in the device can be configured as pneumatic, media separated membrane valves. The valve can be arranged, virtually free of dead spaces, in the measurement circuit. Furthermore, the valves can be installed by means of clamp connectors, in order to enable replacement of individual valves.

All the existing welded connections of the device which are in contact with the testing medium (that is to say the fluid) can be formed as orbital welds, in particular with a nominal pipe diameter DN10 according to DIN32676.

The sensor system as well as the entire measuring arrangement can have protection against overheating.

A housing closure of the device can be arranged in a receptacle with electrically controllable linear guides. The linear guides can be adjusted on the frame of the device in an XY direction and can be securely screwed. As a result, centering of the closure of the device in the region of its locking means is possible.

The device can be rigid, and in particular the measurement circuit can have a rigidity in order to avoid design-related volume changes which falsify measurement values. For this purpose, the air-venting valve can be, for example, rigidly connected to the housing cover of the device.

The device can be designed so that wear parts and/or sensors are easily accessible and, if need be, can be simply removed. This simplifies maintenance and/or calibration work. For this purpose, for example, coded confusion-proof plug connections can be used and/or replaceable plates for the necessary sensor system.

The evaluation means can have an operating panel with optical good/poor display and an integrated USB connector for a possible later use of barcode readers at each station. The evaluation means can be connected to TCP-IP via an Ethernet interface.

The vessel 1 can have a filling level indicator which is arranged in the lowest point of the housing of the vessel 1. Thus the filling level indicator can check whether the test housing is completely emptied.

A temperature sensor, by which the temperature of the testing medium, i.e. the fluid, can be monitored, can be arranged in the region of the pressure measurement cell 4. The pressure measurement cell 4 can have a stepping motor, by means of which a filling level check of the pressure measurement cell 4 can be carried out.

The vessel 1 can have a filling volume which is adapted to specific filter elements to be tested. In this case the filling volume of the vessel can be kept as small as possible in order to save on fluid, which can be discarded after every test. The vessel can be designed using blind volumes for small overall heights.

The test process can be initiated using two manual switches. Suitable safety equipment can ensure that no body parts of an operator are located between the test housing and the locking means.

The vessel 1 can be ventilated by means of a vessel air-vent conduit 7. The vessel air-vent conduit 7 can be regulated by means of an air-venting valve V1.3 of the vessel.

In a similar manner air can be vented from the pressure measurement cell 4 by means of a pressure measurement cell air-vent conduit 8. The pressure measurement cell air-vent conduit 8 can be regulated by means of an air-venting valve V2.1 of the pressure measurement cell.

The evaluation unit can use a measurement algorithm which is under software control and contains a PLC. In this case the pressure measurement cell 4 can be controlled so that it records a continuous series of measurements, which registers the measured values of pressure, absolute volume and temperature. The number and time sequence of the individual measured values can be predetermined by means of the software. For each measurement time a sliding, incremental volume flow, of which the curve shape over time is degressively falling, can be calculated from the individual measured values of the absolute volume per unit of time. This can be used as an integrity characteristic variable for the filter element to be tested.

The pressure measurement cell 4 can likewise be filled by means of the fluid conduit 5. The pressure measurement cell 4 should only be filled if no measurement is carried out. The pressure measurement cell 4 can have a stepping motor having an incremental position indicator. The incremental position indicator can signal to the evaluation unit when the pressure measurement cell 4 no longer has sufficient fluid in order to continue the measuring operation. Thus the incremental position indicator can indicate that the pressure measurement cell 4 must be topped up. In this situation the next regularly due filling operation can be prevented by a corresponding signal until there is no longer any measurement due within a three-way module in question.

The integrity of the filter element F is tested if the vessel 1 in which the filter element F is arranged is connected by means of the vessel valve V1.2. associated therewith to the pressure measurement cell 4. In this case the volume flow and/or the change of volume flow which is required in order to maintain the test pressure in the vessel 1 of the filter element F is measured on the pressure measurement cell 4. In this case either the precisely calculated volume can be determined, and/or a number of incremental steps or indices are used for determination on the motor of the pressure measurement cell 4. The measured volume flow and/or the change of volume flow can be compared on the evaluation means with limit values predetermined by enveloping curves. From this a final predicted integrity characteristic variable can be determined for the expected continuous volume flow of the fluid which occurs for maintenance of the specific test pressure in the first vessel 1. In this case the position and the mathematical description of the enveloping curves can be characteristic for the filter type of the filter element in question. One or more enveloping curves can also be determined with reference to reference measurement data of reference filter elements and can be used for the above-mentioned comparison.

Determining an Integrity Characteristic Variable for the Filter Element

An integrity characteristic variable is determined for the filter element F arranged in the vessel 1. As the integrity characteristic variable it is possible to use, for example, the volume flow through the filter element F which occurs during compacting of the filter element F to a test pressure. The volume flow relates to the volume of fluid flowing through the filter element F. The volume flow can be read off directly at the fluid feed, i.e. for example the pressure measurement cell 4.

In the method first of all any valves which may be present are opened and the fluid is introduced. In this case the vessel as well as the device used for carrying out the method are ventilated. Amongst other this, in this case the pressure measurement cell fills and the compacting of the filter element begins.

Subsequently by means of the stepping motor of the pressure measurement cell a specific test pressure of, for example, approximately 2.5 bars, is set. In this case the incremental steps of the stepping motor can specify the volume necessary for maintaining the specific test pressure in the vessel. In this way the volume as well as the volume flow can be directly detected. The incremental steps or the index of a pressure measurement cell (as special fluid feed) can be configured, for example, in approximately 1 µl (or smaller) steps and thus are very precise.

FIG. 2 shows in a diagram an example of the characteristic of the volume flow through such a filter element in milliliters (ml) per unit of time in minutes (min). The illustrated rhombuses show measurement results on an exemplary filter element BH4.

Already at a first time t1 (in the exemplary embodiment after approximately 0.36 min) a first gradient s1 of the volume flow occurs, which is approximately s1=1.6 g/min. At a later, second time t2 (in the exemplary embodiment after approximately 0.72 min) a second gradient s2 of the volume flow occurs, which is approximately s2=0.2 g/min. In this case the second gradient s2 is significantly less than the first gradient s1. In general, in a filter element having integrity it may be expected that the gradient of the volume flow decreases during compacting.

For comparison, in FIG. 2 an example of a characteristic of the volume flow is shown, which after a start time maintains a gradient s3=1.6 g/min. This characteristic of the volume flow indicates that the filter element does not have integrity. Therefore, at the second time t2 the volume flow of the filter element lacking integrity is already substantially above the volume flow characteristic of a filter element of the same type.

Thus in this example it is already possible at the second time t2 to draw a conclusion as to whether or not the filter element will pass the integrity test.

In particular, in this case, the integrity characteristic variable as the volume flow increases is determined, and thus long before this the filter element is compacted and an almost continuous volume flow of fluid through the filter element occurs, which is required for maintenance of the specific test pressure in the vessel.

The estimation of the integrity characteristic variable can take place, for example, when a specific curvature of the volume flow is reached. In this case the curve shape of the volume flow can be compared with a comparison curve to be expected. In this case a plurality of measured values can be determined over time and are compared with the associated comparative values. The measured values can be determined at defined time intervals.

At least one characteristic of the measurement curve such as, for example, absolute value, gradient, standard deviation, deviation from average values, etc., can be compared with reference or comparative values. Likewise, a plurality of such characteristics can be compared with reference or comparative values. During the comparison a correlation can be determined between measured values and previously known comparative values. In this case in particular a scattering or standard deviation can be evaluated.

The measured values can be compared, for example, with enveloping curves. This is sensible, in particular, in the case of scattered measured values. In this case enveloping curves which run towards one another can be used, of which the spacing relative to one another decreases over time. The scattering of the measured values should likewise decrease as the compacting of the filter element proceeds, and for this reason in particular enveloping curves which run towards one another or converge or progressively come closer relative to one another enable a good comparison.

FIG. 3 shows in a diagram the progression over time of the volume flow of five different filter elements over a somewhat longer time period. In this case the volume flow of two filter elements F1 and F2 rises relatively quickly and relatively high, to over 4 ml/min, and remains at a constant high value. These two tested filter elements F1 and F2 lack integrity, which can be indicated by the volume flow which occurs.

The volume flow of three other filters is likewise shown in the diagram of FIG. 3. The volume flow of the filters F3, F4 and F5 initially rises substantially, reaches a maximum and then decreases again, and subsequently after a while an almost constant volume flow significantly below 1 ml/min occurs. These three filters F3-F5 have integrity and will pass an integrity test.

The measurements on the five tested filter elements F1-F5 were started in a chronologically staggered manner, which is why the volume flows thereof start to increase at different times.

FIG. 4 shows the fed volume of fluid pressed into different filter elements BH2, BH3, BH4 and BH9. In a trial fluid at a test pressure of 2.5 bars was pressed into the vessel. The volume is shown on a logarithmic scale in ml and initially increases substantially, whilst after a short time period it remains almost constant (on the logarithmic scale).

FIG. 5 shows, in a long-term diagram, the volume flow through filter elements BH2, BH3, BH4, BH5 and BH9 determined in the same trial. The volume flow is likewise shown on a logarithmic scale and decreases quickly and substantially.

As shown in the drawings, the volume flow through the filter and/or the volume of the pressed-through filter can be used as an example of an integrity characteristic variable of the filter element. Even while the volume flow is changing, in particular even while the volume flow is increasing, it is already possible to determine the integrity characteristic variable for the filter element. This significantly increases the speed of the method.

CIP Process

The complete device can occasionally be subjected to a "cleaning in place" process, abbreviated to CIP process. This serves to prevent contamination of the system which can be operated with RO water as fluid. The CIP process can begin with complete emptying of all the device parts. Next the device is sterilized by steaming for 20 minutes with steam at a temperature of between approximately 110° C. and approximately 130° C., in particular approximately 121° C. Next the device is cooled by means of compressed air and is rinsed with RO water. As a result, the device is set into the regular operational state.

The emptying of the system can take place, as in the regular testing method, by means of compressed air at 0.8 barg, wherein the pressure measurement cell 4 is also completely emptied.

In this case the steam can be guided onto all components of the device which come into contact with the testing medium (i.e. the RO water). For this purpose, a cylinder of the pressure measurement cell 4 can be fully opened. Any condensate from the steam conduit collecting during steaming is drawn off immediately before the steaming by means of a condensate separator at the steam inlet.

Due to the cooling with compressed air up to approximately 80° C. a sudden negative pressure formation is avoided by a condensation process of the residual steam remaining in the system.

Parameters of an Exemplary Embodiment

Some process parameters for a device according to an exemplary embodiment are set out below:
operating pressure of approximately 6 barg overpressure;
test pressure at approximately 2.5 barg overpressure;
fluid inflow of RO water;
waste water connection with siphon and drain valve V20;
steam inflow with steaming at 124° C. and at 2.5 bar, corresponding to 1.5 barg overpressure;
Ethernet network connection;
230 Volt connection;
data output as printed measurement value protocol including the program parameters used and the order data such as material, order number and batch number, for example as a *.txt file;
interface for a database connection, for example by means of SQL, in order by means of the database to be able to manage test programs centrally for a plurality of systems in use, and for storage of the measured values.

LIST OF REFERENCE SIGNS 1 vessel
4 pressure measurement cell (fluid feed)
5 fluid conduit
6 drain conduit
7 vessel air-vent conduit
8 pressure measurement cell air-vent conduit
9 pressure measurement cell controller
10 outlet conduit
11 fluid inflow
15 temperature sensor
16 device
F filter element
F1, F2, F3, F4, F5 filter element
BH2, BH3, BH4, BH5, BH9 filter element
V1.1 fluid inlet valve
V1.2 vessel valve
V1.3 outlet valve
V1.4 air-vent valve of the vessel
V2.1 air-vent valve of the pressure measurement cell
s1 first gradient
s2 second gradient
s3 third gradient
t1 first time
t2 second time

The invention claimed is:

1. A method for carrying out an integrity test on a filter element, comprising the steps of:
arranging a filter element (F) to be tested in a vessel (1),
filing the vessel (1) with a fluid to achieve a predetermined specific test pressure that is sufficient to compact the filter element (F) and to achieve a substantially continuous volume flow after a specified time,
performing a rough test by monitoring a fluid flow from the vessel (1) before reaching the specific test pressure, identifying a defective filter element if the fluid flow from the vessel exceeds a rough test limit before reaching the specific test pressure, maintaining the specific test pressure in the vessel (1) with controlled replenishment of fluid into the vessel (1) and/or with a controlled change in internal volume of the vessel (1), determining an integrity characteristic variable for the filter element (F) in a manner dependent on the controlled replenishment of fluid into the vessel (1) and/or in a manner dependent on the controlled change in internal volume of the vessel (1) before reaching the specified time that is sufficient to compact the filter element (F) and to achieve the substantially continuous volume flow of fluid that is required for maintaining the specific test pressure in the vessel (1).

2. The method of claim 1, wherein the integrity characteristic variable is dependent upon at least one characteristic of the volume flow of fluid that is required for maintenance of the specific test pressure in the vessel (1).

3. The method of claim 1, wherein the integrity characteristic variable is determined within a maximum of nine minutes after the start of filling of the vessel (1).

4. The method of claim 1, wherein the step of maintaining the specific test pressure in the vessel (1) further comprises using a pressure measurement cell (4) to achieve a controlled replenishment of fluid into the vessel (1).

5. The method of claim 4, the step of using a pressure measurement cell (4) comprises using a stepping motor of the pressure measurement cell (4) to actuate a pressure piston so that the specific test pressure is maintained in the vessel (1).

6. The method of claim 1, wherein the step of maintaining the specific test pressure in the vessel (1) further comprises penetrating a displacement body into the vessel (1) to achieve a controlled change in internal volume of the vessel (1).

7. The method of claim 1, wherein the integrity characteristic variable is determined by a mathematical estimation.

8. The method of claim 7 wherein the integrity test is ended when the estimation shows that, with a predetermined probability, the filter element (F) to be tested will or will not pass the integrity test.

9. The method of claim 7, wherein the estimation takes place by a mathematical prediction of a volume flow of the fluid that occurs by means of enveloping curves, wherein the enveloping curves are coordinated with the filter element (F) to be tested.

10. The method of claim 1, wherein the step of maintaining the specific test pressure in the vessel is achieved by the controlled replenishment of fluid into the vessel (1) and takes place with a precision of less than approximately 10 µl.

11. The method of claim 1, wherein the integrity characteristic variable is dependent upon a volume flow through the filter element (F) per unit time while maintaining the specific pressure and before reaching the specified time that is sufficient to compact the filter element (F).

12. A device for carrying out an integrity test on a filter element, with a vessel (1) in which the filter element (F) to be tested can be arranged, the device comprising:

at least one conduit (5), by which a fluid can be introduced into the vessel so that the pressure of the fluid can be set to a specific test pressure, a fluid feed (4) that maintains the specific test pressure in the vessel (1) by replenishing the fluid feed into the vessel (1) in a controlled manner and/or changes the internal volume of the vessel in a controlled manner, and an evaluation means that determines, in a manner dependent on the controlled replenishment of fluid into the vessel (1) and/or in a manner dependent on the controlled change in internal volume of the vessel (1), an integrity characteristic variable for the filter element (F) before attaining a substantially continuous volume flow of fluid that occurs after a specified time that is required to compact the filter element (F) and to maintain the specific test pressure in the vessel (1).

13. The device of claim 12, wherein the evaluation means estimates the integrity characteristic variable in dependence upon at least one characteristic of the volume flow of fluid that is required for maintenance of the specific test pressure.

14. The device of claim 12, wherein the fluid feed (4) comprises a pressure measurement cell (4) having a stepping motor that actuates a pressure piston so that the specific test pressure in the vessel (1) is substantially maintained, wherein the evaluation means uses a step number of the stepping motor of the pressure measurement cell (4) as a characteristic quantity of the volume of fluid that flows through the filter element (F) to maintain the specific test pressure.

15. The device of claim 12, wherein the fluid feed comprises a displacement body that penetrates in a controlled manner into the vessel (1) and thereby changes the internal volume of the vessel (1).

16. The device of claim 12, wherein the device has a pressure reducer and/or a flow reducer, that reduces the pressure and/or the flow of the fluid in a filling conduit (5).

17. The device of claim 12, wherein the fluid feed (4) replenishes fluid into the vessel (1) with a precision of 0.1 µl to 10 µl and/or changes the volume of the vessel with a precision of 0.1 µl to 10 µl.

18. A method for carrying out an integrity test on a filter element, comprising the steps of:

filling at least one vessel (1), in which a filter element (F) to be tested is arranged, with a fluid, setting the pressure of the fluid in the vessel (1) to a predetermined specific test pressure, maintaining the specific test pressure in the vessel (1) with a controlled change in internal volume of the vessel (1) by penetrating a displacement body into the vessel (1), determining an integrity characteristic variable for the filter element (F) in a manner dependent on the controlled change in internal volume of the vessel (1) before reaching a substantially continuous volume flow of fluid that is required for maintaining the specific test pressure in the vessel (1).

\* \* \* \* \*